(12) United States Patent
Liu

(10) Patent No.: US 11,439,323 B2
(45) Date of Patent: Sep. 13, 2022

(54) SMART PATCH AND METHOD FOR FABRICATING THE SAME

(71) Applicant: BOE Technology Group Co., Ltd., Beijing (CN)

(72) Inventor: Kairan Liu, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 199 days.

(21) Appl. No.: 16/240,022

(22) Filed: Jan. 4, 2019

(65) Prior Publication Data

US 2019/0328285 A1 Oct. 31, 2019

(30) Foreign Application Priority Data

Apr. 28, 2018 (CN) .......................... 201810399237.X

(51) Int. Cl.
 *A61B 5/11* (2006.01)
 *A61B 5/00* (2006.01)
 *A61M 37/00* (2006.01)

(52) U.S. Cl.
 CPC .......... *A61B 5/1118* (2013.01); *A61B 5/6801* (2013.01); *A61M 37/0015* (2013.01); *A61M 2037/0023* (2013.01); *A61M 2037/0046* (2013.01); *A61M 2037/0061* (2013.01); *B81B 2201/055* (2013.01)

(58) Field of Classification Search
 CPC ...... A61M 37/0015; A61M 2037/0023; A61M 2037/0046; A61M 2037/0061; A61M 2037/003; A61M 2037/0053; A61B 5/1118; A61B 5/6801; A61B 5/6833; A61B 5/746; A61B 5/4839; B81B 2201/055

See application file for complete search history.

(56) References Cited

U.S. PATENT DOCUMENTS

2008/0009800 A1 1/2008 Nickel
2008/0269685 A1* 10/2008 Singh .................. A61K 38/385
                                                604/173

(Continued)

FOREIGN PATENT DOCUMENTS

CN   101068591 A   11/2007
CN   101553275 A   10/2009

(Continued)

OTHER PUBLICATIONS

Office Action for corresponding Chinese Application 201810399237.X dated Jun. 22, 2020.

(Continued)

*Primary Examiner* — Amber R Stiles
*Assistant Examiner* — Avery Smale
(74) *Attorney, Agent, or Firm* — ArentFox Schiff LLP; Michael Fainberg

(57) ABSTRACT

A smart patch and a method for fabricating the same are provided. The smart patch includes: a substrate, a detecting component arranged on the substrate, and a reminding component connected with the detecting component, wherein the detecting component is configured to detect a stretch degree of the substrate; and the reminding component is configured to transmit a reminding signal when the stretch degree of the substrate, detected by the detecting component, meets a preset condition.

8 Claims, 4 Drawing Sheets

(56) References Cited

U.S. PATENT DOCUMENTS

| | | | | |
|---|---|---|---|---|
| 2012/0027837 A1* | 2/2012 | DeMuth | ............... | C12N 5/0068 |
| | | | | 424/443 |
| 2014/0336487 A1 | 11/2014 | Wang et al. | | |
| 2017/0147789 A1* | 5/2017 | Wiedenhoefer | ........ | G16H 40/67 |
| 2020/0009767 A1 | 1/2020 | Li | | |

FOREIGN PATENT DOCUMENTS

| | | | | |
|---|---|---|---|---|
| CN | 103301563 | A | 9/2013 | |
| CN | 104114224 | A | 10/2014 | |
| CN | 104117137 | A | 10/2014 | |
| CN | 205007427 | U | 2/2016 | |
| CN | 105427551 | A | 3/2016 | |
| CN | 205072831 | U | 3/2016 | |
| CN | 105833424 | A | 8/2016 | |
| CN | 106727273 | A | 5/2017 | |
| JP | 6255759 | B2 | 1/2018 | |
| TW | I455709 | B | 10/2014 | |
| WO | WO-2017090254 | A1 * | 6/2017 | ............. B29C 39/00 |

OTHER PUBLICATIONS

Chinese Office Action for corresponding Application 201810399237.X dated Sep. 15, 2021.

\* cited by examiner

SMART PATCH AND METHOD FOR FABRICATING THE SAME

CROSS-REFERENCES TO RELATED APPLICATIONS

This application claims priority to Chinese patent application No. 201810399237.X filed on Apr. 28, 2018, which is incorporated herein by reference in its entirety.

FIELD

The present disclosure relates to the field of display technologies, and particularly to a smart patch and a method for fabricating the same.

BACKGROUND

In daily life, a number of rectifying devices have been designed to prevent some part of a human body from being bent for a long period of time. For example, the BABAKA® products have been designed to prevent the back of a human body from being bent for a long period of time, which would otherwise have resulted in a humpback. However the traditional BABAKA® products are so heavy and discomfortable that users are reluctant to wear the products for a long time and also hindered from wearing their usual clothing. Stated otherwise, the devices for rectifying a part of a human body from being bent in the related art are generally heavy and discomfortable, and can not provide a smart reminder.

SUMMARY

In one aspect, an embodiment of the disclosure provides a smart patch. The smart patch includes: a substrate, a detecting component arranged on the substrate, and a reminding component connected with the detecting component, wherein the detecting component is configured to detect a stretch degree of the substrate; and the reminding component is configured to transmit a reminding signal when the stretch degree of the substrate, detected by the detecting component, meets a preset condition.

In some embodiments, the detecting component is configured to have its resistance increasing as the substrate is being stretched, to thereby detect the stretch degree of the substrate; and the reminding component is configured to transmit the reminding signal when the resistance exceeds a preset value, and/or the resistance has exceeded a second preset value for a time length longer than a preset time length, wherein the first preset value is more than the second preset value.

In some embodiments, the detecting component includes a piezo-resistive pressure sensor.

In some embodiments, the substrate is further provided with a plurality of micro-needles on a surface thereof for contact with a human body, and each of the micro-needles includes at least one shell, and a medicine surrounded by the shell, wherein: the micro-needle is configured, when puncturing into to a skin, to enable at least a part of the shell to be hydrolyzed so that the medicine in the shell contacts with tissue fluid of the human body.

In some embodiments, each of the micro-needles includes one shell, and the same medicine is arranged in the shell of each of the micro-needles.

In some embodiments, each of the micro-needles includes one shell, a first medicine is arranged in the shells of a part of the micro-needles, and a second medicine is arranged in the shells of the other micro-needles, wherein the first medicine and the second medicine are different medicines.

In some embodiments, each of the micro-needles includes two shells which are a first shell, and a second shell located inside the first shell, wherein first medicine is arranged between the first shell and the second shell, and second medicine is arranged in the second shell, wherein the first medicine and the second medicine are different medicines.

In some embodiments, each of the micro-needles includes three shells, which are a first shell, a second shell located inside the first shell, and a third shell located inside the second shell, wherein a first medicine is arranged between the first shell and the second shell, a transition chamber is arranged between the second shell and the third shell, and a second medicine is arranged in the third shell, wherein the first medicine and the second medicine are different medicines.

In some embodiments, the first medicine is a water absorbing medicine, and the second medicine is an anti-inflammatory medicine.

In some embodiments, the material of the shell includes a nanometer fiber.

In some embodiments, a shape of each of the micro-needles is a triangular pyramid, a rectangular pyramid, or a circular cone, wherein a bottom of the triangular pyramid, the rectangular pyramid, or the circular cone contacts with a bottom of the substrate.

In some embodiments, a length of each of the micro-needles in a direction perpendicular to the substrate ranges from 100 μm to 200 μm.

In some embodiments, the substrate is nanometer paper.

In another aspect, an embodiment of the disclosure further provides a method for fabricating the smart patch according to any one of the embodiments above. The method includes: forming the substrate; and forming the detecting component on the substrate, and the reminding component connected with the detecting component.

In some embodiments, the substrate is further provided with a plurality of micro-needles on a surface thereof for contact with a human body; and the forming the substrate includes: pouring nanometer cellulose dispersion liquid into a first mold having an array of hollow micro-needles; inserting a second mold having a corresponding array of micro-needles into the first mold containing the nanometer cellulose dispersion liquid, keeping a preset distance between the second mold and the first mold in a vertical direction, and drying and shaping them, wherein the second mold is provided with pads respectively on two sides of a frame thereof so that a preset distance is kept between the second mold and the first mold in the vertical direction when the second mold is arranged opposite to the first mold; removing the second mold; placing the medicine into cavities of the micro-needles formed by the shaped nanometer cellulose dispersion liquid, and drying it; pouring nanometer cellulose solution, and mold-pressing and drying it using a planar third mold; and removing the third mold and the first mold.

DETAILED DESCRIPTION

Figure 1:
FIG. 1 is a schematic structural diagram of a smart patch according to an embodiment of the disclosure.

Implementations of the embodiments of the disclosure will be described below in details with reference to the drawings. It shall be noted that identical or like reference numerals refer to identical or like elements, or elements with identical or like functions throughout the drawings. The embodiments to be described below with reference to the drawings are illustrative, and only intended to explain the disclosure, but not to limit the disclosure thereto.

Referring to FIG. 1, an embodiment of the disclosure provides a smart patch. The smart patch includes: a substrate 1, a detecting component 2 arranged on the substrate 1, and a reminding component 3 connected with the detecting component 2. When the substrate 1 of the smart patch is attached to a body part, the substrate 1 can be stretched as the body part is being bent.

The detecting component 2 is configured to detect the stretch degree of the substrate.

The reminding component 3 is configured to transmit a reminding signal when the stretch degree of the substrate meets a preset condition.

Where the reminding component 3 is configured to transmit a reminding signal when the stretch degree of the substrate meets a preset condition, which refers to that the stretch degree of the substrate exceeds a preset degree, and/or the time length of the stretch of substrate exceeds a preset time length.

A smart patch according to an embodiment of the disclosure includes: a substrate, a detecting component arranged on the substrate, and a reminding component connected with the detecting component. When the substrate of the smart patch is attached to a body part, the substrate can be stretched as the body part is being bent; the detecting component can detect the stretch degree of the substrate; and the reminding component can transmit a reminding signal when the stretch degree of the substrate meets a preset condition. Furthermore when the smart patch is attached to some body part which is bent frequently, when the body part is bent to a significant degree, or although the body part isn't bent to an insignificant degree, it has been bent for a long time, then a reminding signal may be transmitted so that a user can be reminded smartly of a change to this bent posture, so as to avoid the human body from being injured when the body part had been bent for a long time. Moreover the smart patch according to the embodiment of the disclosure has a small overall volume and a low weight, and is comfortable.

In some embodiments, the detecting component 2 has its resistance increasing as the substrate 1 is being stretched, to thereby detect the stretch degree of the substrate 1; and the reminding component 3 transmits the reminding signal when the resistance exceeds a preset value, and/or the resistance has exceeded a second preset value for a time length longer than the preset time length, where the first preset value is more than the second preset value.

In some embodiments, the detecting component 2 includes a piezo-resistive pressure sensor. In the embodiment of the disclosure, the bend degree of the body part can be characterized by variance of the resistance of the detecting component, and the reminding component can transmit the reminder so that when the body part is bent to a significant degree, or has been bent for a longer time length, the user can be reminded. Of course, the detecting component can alternatively be another component which can detect the stretch degree of the substrate, and for example, a stress in the substrate is varying as the substrate is being stretched, so a detecting component detecting a pulling force can also detect the stretch degree of the substrate, although the embodiment of the disclosure will not be limited thereto.

Figure 2:
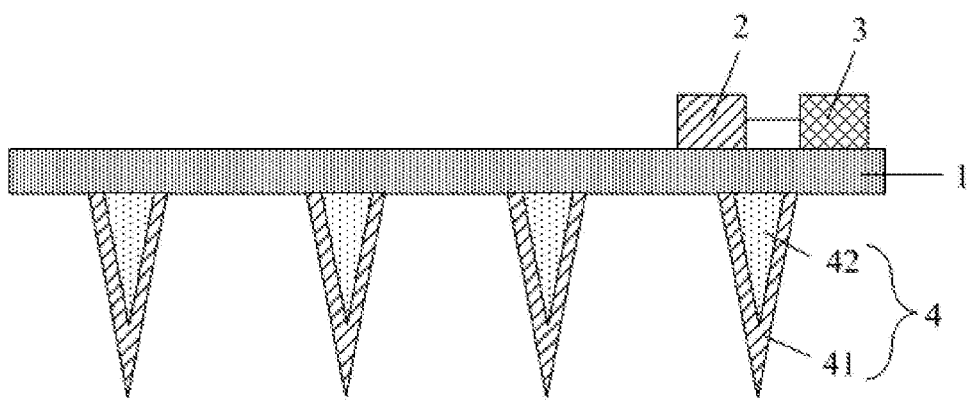
FIG. 2 is a schematic structural diagram of the smart patch arranged with micro-needles according to the embodiment of the disclosure.

In some embodiments, referring to FIG. 2, the substrate are further provided with a plurality of micro-needles 4 on the surface thereof for contact with the human body, and each micro-needle 4 includes one or more shells 41, and a medicine 42 located in the shell 41. When the micro-needle 4 punctures into the skin, at least a part of the shell 41 is hydrolyzed so that the medicine 42 in the shell 41 contacts with tissue fluid of the human body. As compared with a plaster patch in the related art, the micro-needles can be arranged in the smart patch according to the embodiment of the disclosure to puncture into the skin of the human body directly, for example, puncture into the active epidermal layer, so that the medicine can be absorbed more effectively. In a specific implementation, the crystallinity of the micro-needles can be adjusted so that they are more hydrolysable, so when they enter the tissue fluid, they can be hydrolyzed completely, and release the medicine therein. Alternatively the capacities of respective components of the shell of the micro-needle 4 to absorb water can be changed so that the bottoms of the micro-needles can be hydrolyzed significantly, and thus they can be broken at their bottoms, and become separate capsules which enter the tissue fluid of the human body.

In a specific implementation, the number of shells 41 in each micro-needle 4 can be set as needed in reality, which will be described below by way of an example.

For example, referring to FIG. 2, each micro-needle 4 includes a shell 41, and the same medicine 42 is arranged in each shell 41.

In reality, a neck becomes stiffen because a muscle thereof has been excessively contracted constantly so that the muscle of the neck is provided with less blood, but also a metabolite, e.g., lactic acid, etc., is accumulated, so the ischemic muscle is sore. In some embodiments of the disclosure, the material of the shell of each micro-needle is a nanometer fiber, where the nanometer fiber usually includes a plurality of hydroxyls, and the cellulose includes linear molecules without any branch, so that the hydroxyls on a chain of the cellulose tend to be arranged in order, and a large number of hydrogen bonds are formed into an ordered mesh fabric; and in this way, natural cellulose fibers are further bonded together densely in order into a dense, stable, and indecomposable crystal fabric of the cellulose. As opposed to a crystal area of the cellulose in the crystal fabric in the cellulose, an area thereof which does not appear in an ordered crystal fabric is a non-crystal area or an amorphous area. The cellulose in the crystal area is highly stable and difficult to decompose, and the non-crystal area tends to come into contact with other molecules, and to be decomposed. The lactic acid is an organic substance of small molecules, its carboxyl releases a proton in aqueous solution, the molecules in the non-crystal area of the cellulose are arranged loosely, infiltrating acid is ionized, and produces $H^+$ to catalyze breaking of indicant bonds of the molecule chain of the cellulose, so that the amorphous area is disturbed, and thus the cellulose is decomposed, so at least a part of the shell of each micro-needle is decomposed, and the medicine in the micro-needle can be released into the tissue fluid. In the embodiment of the disclosure, each micro-needle 4 is arranged with a shell 41, and the same medicine is arranged in each micro-needle 4; and specifically medicine for activating blood circulation and dredging meridians and collaterals can be arranged in each micro-needle, so that when the neck is sore, the smart patch according to the embodiment of the disclosure can be attached to the neck, so that the medicine arranged in the micro-needles can be released into the tissue fluid to thereby alleviate the stiffen neck from being sore.

Figure 3:
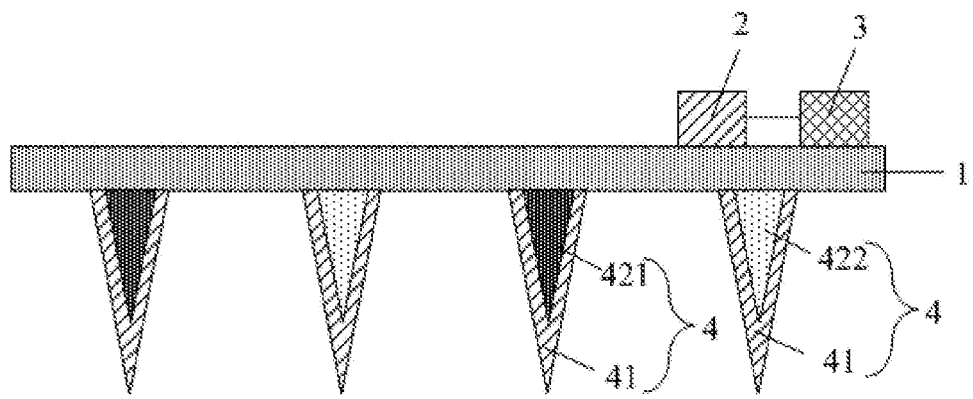
FIG. 3 is a schematic structural diagram of the smart patch arranged with different medicines according to the embodiment of the disclosure.

In some embodiments, referring to FIG. 3, each micro-needle 4 includes a shell 41, first medicine 421 is arranged in the shells 41 of a part of the micro-needles 4, and second medicine 422 is arranged in the shells 41 of the other micro-needles 4, where the first medicine 421 and the second medicine 422 are different medicines. The micro-needle 4 provided with the first medicine 421 and the micro-needle 4 provided with the second medicine 422 can be arranged alternately. In a real application, for example, a bleb tends to be formed due to scalding, so in the smart patch according to the embodiment of the disclosure, each micro-needle 4 is provided with a shell 41, where a water absorbing medicine can be arranged in a part of the micro-needles 4, that is, the first medicine 421 is a water absorbing medicine, and an anti-inflammatory medicine is arranged in the other micro-needles 4, that is, the second medicine 422 is an anti-inflammatory medicine; and in this manner, the bleb is punctured using the micro-needles 4 of the smart patch, so that the water absorbing which is arranged in the part of the micro-needles 4 can enable tissue fluid in the bleb to suck the patch automatically, and the anti-inflammatory medicine arranged in the other micro-needles 4 can treat the scald site, that is, in the smart patch according to the embodiment of the disclosure, the different medicines can be arranged in the different micro-needles to thereby better treat corresponding symptoms in specific instances so as to achieve a better treatment effect. Furthermore there is such a small wound incurred by the micro-needles that the bleb cannot contact with an external environment throughout the treatment, and thus can be avoided from being infected while breaking, so that the site where the bleb is formed can get well rapidly. Additionally, temperature and humidity sensors can be arranged in the patch, and since the concrescence and the infection condition of a wound are dependent upon the temperature, the humidity, and the PH condition, these parameters can be monitored to thereby monitor the concrescence and the infection condition of the wound. It shall be noted that even if the human body sometimes excretes little lactic acid or pyruvic acid, then the shells of the micro-needles made of the nanometer fiber may be decomposed slowly in the environment inside the human body, so that the medicines in the shells can contact with the tissue fluid.

Figure 4:
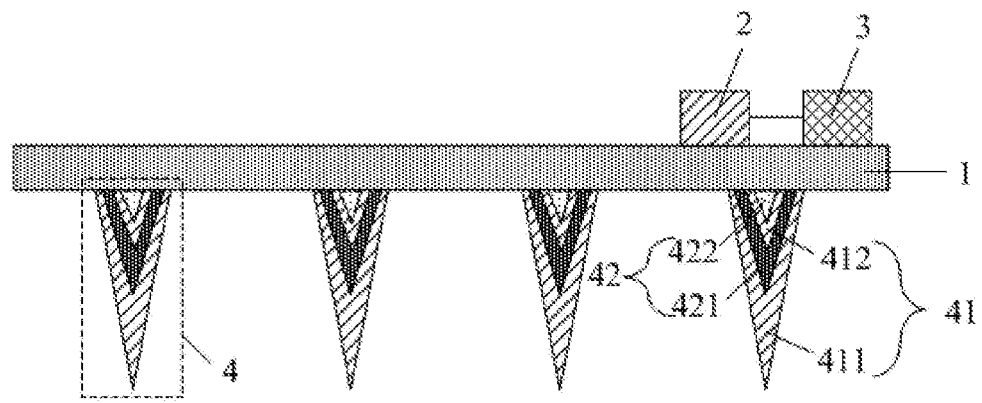
FIG. 4 is a schematic structural diagram of the smart patch including the micro-needles arranged with two shells according to the embodiment of the disclosure.

In some embodiments, referring to FIG. 4, each micro-needle 4 includes two shells 41, which are a first shell 411, and a second shell 412, where a first medicine 421 is arranged between the first shell 411 and the second shell 412, and a second medicine 422 is arranged in the second shell 412, where the first medicine 421 and the second medicine 422 are different medicines. In a real application, a bleb, an acne, etc., shall be firstly cleaned, and then inflammation shall be diminished, so in the smart patch according to the embodiment of the disclosure, each micro-needle 4 includes two shells 41, which are a first shell 411, and a second shell 412, where a water absorbing medicine can be arranged between the first shell 411 and the second shell 412, and an anti-inflammatory can be arranged in the second shell 412, so tissue fluid can reach the second shell 412 only after it soaks the first shell 411. In this manner, the aperture ratio of the second shell 412 is increased due to the tissue fluid so that the anti-inflammatory medicine can be released from the second shell 412, and in this way, the medicines can take effect in a precise sequence. With this solution, the medicines can be released after the tissue fluid is cleaned, so that their effects can be maximized. Alike the smart patch according to the embodiment of the disclosure can also be applicable to other scenarios where sequential treatment is desirable, and at this time, the nanometer fiber paper constituting the micro-needles shall be made in a significantly amorphous state so that the micro-needles can suck the normal tissue fluid rapidly, and the medicines can be released from the micro-needles rapidly.

Figure 5:
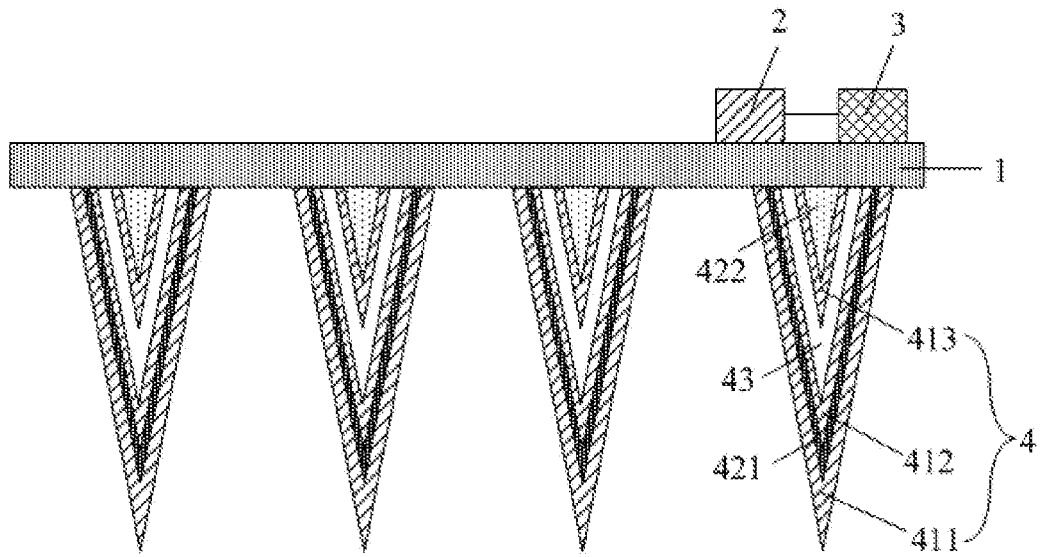
FIG. 5 is a schematic structural diagram of the smart patch including the micro-needles arranged with three shells according to the embodiment of the disclosure.

In some embodiments, referring to FIG. 5, each micro-needle 4 includes three shells 41, which are a first shell 411, a second shell 412 located inside the first shell 411, and a third shell 413 located inside the second shell 412. A first medicine 421 is arranged between the first shell 411 and the second shell 412, and a transition chamber 43 is arranged between the second shell 412 and the third shell 413, where a second medicine 422 is arranged in the third shell 413, the first medicine 421 is different from the second medicine 422. In a real application, in order to preset a time length for releasing the first medicine 421 and the second medicine 422, in the embodiment of the disclosure, the transition chamber 43 with a preset size is arranged between the second shell 412 and the third shell 413 so that the time length for releasing the first medicine 421 and the second medicine 422 can be controlled, so the two medicines can be released at a specific interval of time.

In a specific implementation, the first medicine 421 can be water absorbing medicine, and the second medicine 422 can be anti-inflammatory medicine. Of course, the first medicine 421 and the second medicine 422 can alternatively be other medicines as needed, although the embodiment of the disclosure will not be limited thereto.

In some embodiments, the material of the shells 41 of the micro-needles 4 can be a nanometer fiber.

In some embodiments, the shape of the micro-needle is a triangular pyramid, a rectangular pyramid, or a circular cone, where the bottom of the triangular pyramid, the rectangular pyramid, or the circular cone contacts with the bottom of the substrate. Optionally the length of the micro-needle in the direction perpendicular to the substrate ranges from 100 µm to 200 µm. Since the skin includes three layers, which are horny layer, the viable epidermis layer, and the dermis layer. The thickness of the horny layer approximately ranges from 15 µm to 20 µm, and generally includes corneocytes, keratin, and matrix, but does not include any blood vessel or nerve, can prevent a substance, including a medicine with a high molecule weight, from the outside from entering the human body through the skin; the thickness of the viable epidermis layer located below the horny layer approximately ranges from 130 µm to 180 µm, and includes a small number of living cells and nerves, but does not include any blood vessel; and the deeper dermis layer includes a large number of living cells, nerves, and blood vessels. In the embodiment of the disclosure, the micro-needles can alternatively be fabricated of nanometer paper, the length of the micro-needles ranges from 100 µm to 200 µm, and the micro-needles puncture the viable epidermis layer, but does not puncture the dermis layer, and come into contact with the tissue fluid, but do not come into contact the nerves and the blood vessels, so the user can not fell painful. The micro-needles include blood-activating medicine components. The parts of the micro-needles to puncture into the skin are crystallized to some extent using solution, an ultrasonic wave, etc., so that they can detect $H^+$ generated from the lactic acid and the pyruvic acid, and control the rate at which the medicines in the micro-needles are released, and the amounts of released medicines to increase as the amounts of lactic acid and pyruvic acid are increasing. For example, the levels of the lactic acid and the pyruvic acid are normal in a normal state of the human body, and as this time, the patch releases the medicines at a low rate; and as the muscle is tired, the amounts of lactic acid and pyruvic acid in the muscle are increasing, and the amount of $H^+$ produced as a result of decomposition is also increasing, and at this time, the amorphous area is being decomposed so that a large amount of medicine components in the micro-needles are released from the micro-needles, and being diffused into the tissue fluid at a high rate. In this way, the medicine can better take effect instead of being wasted, thus resulting in a better treatment effect very soon than the existing plasters. Moreover the crystallinity of the micro-needles can be adjusted so that they are more hydrolysable, so when they enter the tissue fluid, they can be hydrolyzed completely, and release all the medicines therein. Alternatively the capacities of respective cellulose components to absorb water can be changed so that the bottoms of the micro-needles can be hydrolyzed significantly, and thus they can be broken at their bottoms, and become separate capsules which enter the tissue fluid of the human body.

In some embodiments, the substrate is nanometer paper. The nanometer fiber is transparent, can be well bonded with the human body, and has good biological compatibility, i.e., breathability.

Figure 6:
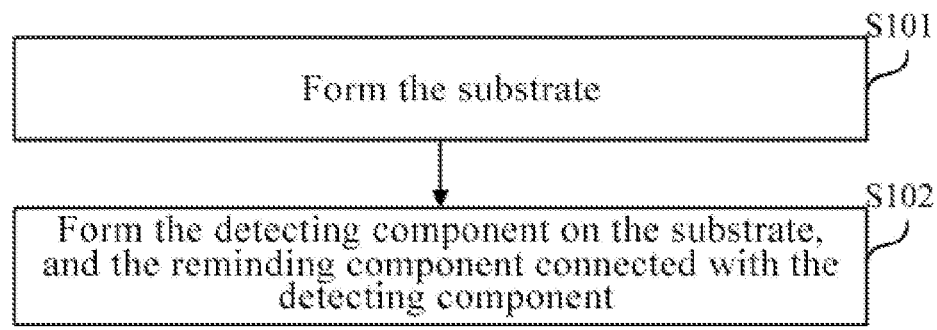
FIG. 6 is a schematic flow chart of fabricating a smart patch according to an embodiment of the disclosure.

Referring to FIG. 6, an embodiment of the disclosure further provides a method for fabricating the smart patch according to the embodiment of the disclosure, where the fabricating method includes the following steps.

The step S101 is to form the substrate.

The step S102 is to form the detecting component on the substrate, and the reminding component connected with the detecting component.

In some embodiments, a plurality of micro-needles are further arranged on the side of the substrate for contact with a human body, and referring to FIG. 7 to FIG. 11, forming the substrate in the step S101 specifically includes the following steps.

Figure 7:
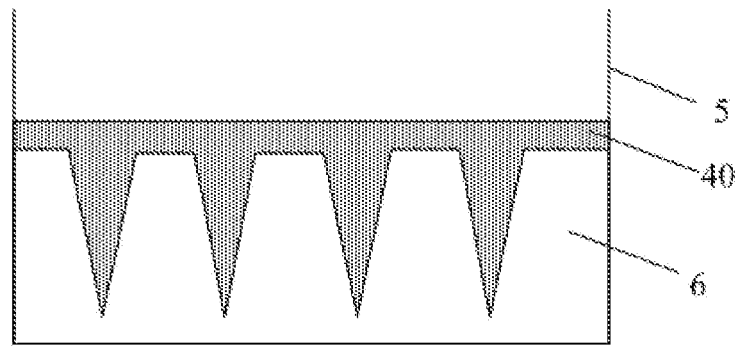
FIG. 7 is a schematic structural diagram after nanometer cellulose liquid is poured into a first mold according to the embodiment of the disclosure.

The step S1011 is to pour nanometer cellulose dispersion liquid 40 into a first mold 6 having an array of hollow micro-needles, where the first mold 6 can be arranged in a container 5, as illustrated in FIG. 7.

Figure 8:
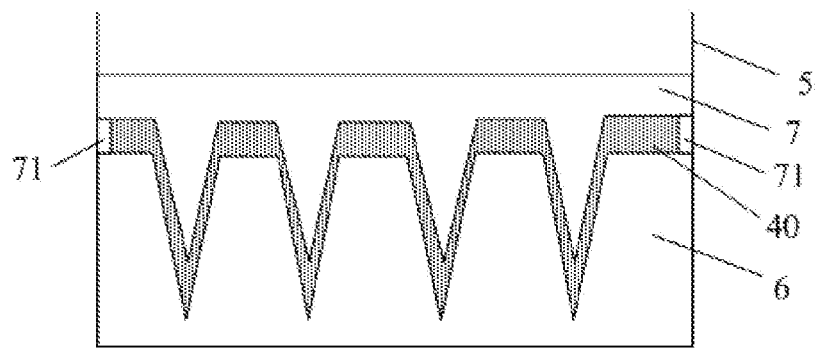
FIG. 8 is a schematic structural diagram after a second mold is placed according to the embodiment of the disclosure.

The step S1012 is to insert a second mold 7 having a corresponding array of micro-needles into the first mold 6 containing the nanometer cellulose dispersion liquid 40, as illustrated in FIG. 8, and keeping a preset distance between the second mold 7 and the first mold 6 in the vertical direction, and drying and shaping them, where the second mold 7 is provided with pads 71 arranged respectively on two sides of a frame of the second mold 7 so that there is a preset distance between the second mold 7 and the first mold 6 in the vertical direction when the second mold 7 is arranged opposite to the first mold 6.

The step S1013 is to remove the second mold.

Figure 9:
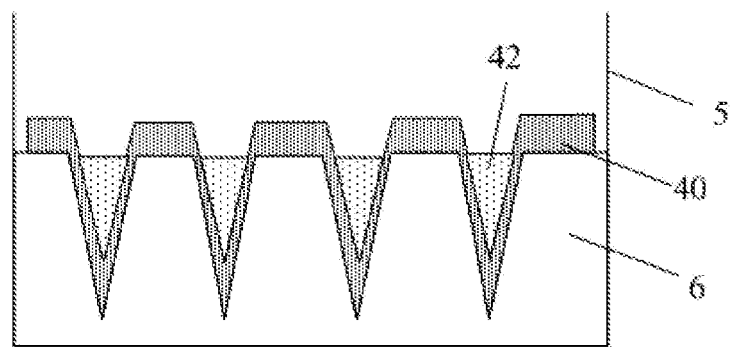
FIG. 9 is a schematic structural diagram after medicines are fabricated according to the embodiment of the disclosure.

The step S1014 is to place the medicine 42 into cavities of the micro-needles formed by the shaped nanometer cellulose dispersion liquid, and to dry, as illustrated in FIG. 9.

Figure 10:
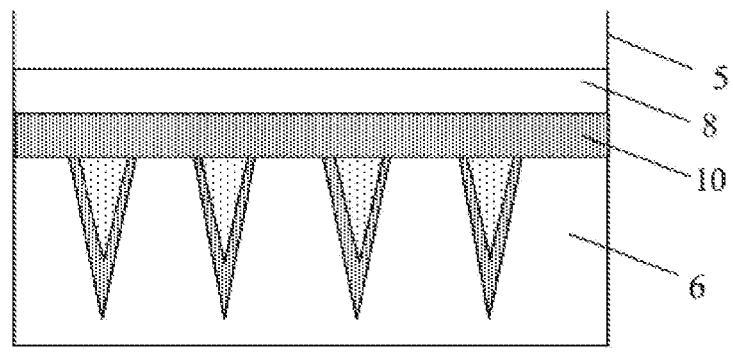
FIG. 10 is a schematic structural diagram after a third mold is placed according to the embodiment of the disclosure.

The step S1015 is to pour nanometer cellulose solution 10, and to mold-press and dry it using a planar third mold 8, as illustrated in FIG. 10.

Figure 11:
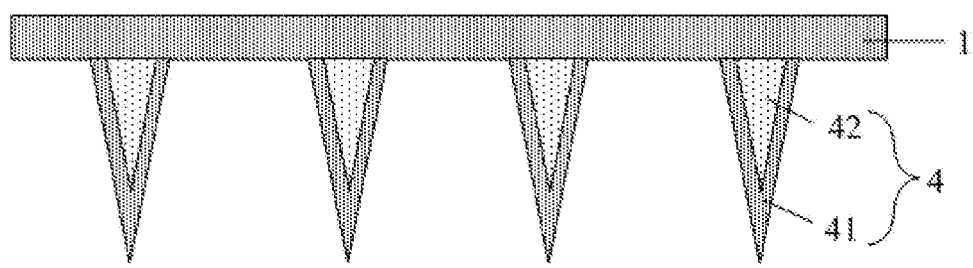
FIG. 11 is a schematic structural diagram of the smart patch fabricated according to the embodiment of the disclosure.

The step S1016 is to remove the third mold 8 and the first mold 6, and to form the substrate 1, and the micro-needles 4 arranged on the substrate 1, as illustrated in FIG. 11.

Since the nanometer paper is experimentally fabricated at present by firstly forming a film on a silicon substrate, and then removing it, the array of micro-needles can be fabricated using the nanometer fiber paper using a plurality of molds in the embodiment of the disclosure. Firstly a mold corresponding to the outer diameter of the micro-needles is fabricated using silicon, PDMS, or another polymer, where the mold is referred to as a first mold, and the shape thereof is the same as the array of hollow micro-needles; and a mold corresponding to the inner diameter of the micro-needles is referred to as a second mold, where the diameter difference between the micro-needles in the second mold and those in the first mold ranges from 20 µm to 30 µm, or can be adjusted as needed in reality. Pads with a size of generally also 20 µm to 30 µm are arranged at specific positions on the second mold and the first mold so that there is some distance between the second mold and the first mold. The nanometer cellulose dispersion liquid with some concentration is poured into the first mold, and at the same time, the second mold is placed, and at this time, the solution is filled up between the two molds; and after it is pressed and shaped using the second mold, it can be dried, thus resulting in planar inner and outer surfaces of the micro-needles, and at this time, medicine power is placed into the cavities of the micro-needles, and then dried, and the nanometer cellulose solution with some concentration is poured and dried, thus resulting in the patch including the array of micro-needles.

Advantageous effects of the embodiments of the disclosure are as follows: a smart patch according to an embodiment of the disclosure includes: a substrate, a detecting component arranged on the substrate, and a reminding component connected with the detecting component, where when the smart patch is attached to a body part, the substrate can be stretched as the body part is being bent; the detecting component can detect the stretch degree of the substrate; and the reminding component can transmit a reminding signal when the stretch degree of the substrate meets a preset condition. Furthermore when the smart patch is attached to some body part which is bent frequently, when the body part is bent to a significant degree, or although the body part isn't bent to an insignificant degree, it has been bent for a long time, then a reminding signal may be transmitted so that a user can be reminded smartly of a change to this bent posture so as to avoid the human body from being injured if the body part had been bent for a long time. Moreover the smart patch according to the embodiment of the disclosure has a small overall volume and a low weight, and is comfortable.

Evidently those skilled in the art can make various modifications and variations to the disclosure without departing from the spirit and scope of this disclosure. Thus the disclosure is also intended to encompass these modifications and variations thereto so long as the modifications and variations come into the scope of the claims appended to the disclosure and their equivalents.

The invention claimed is:

1. A smart patch, comprising: a substrate, a detecting component arranged on the substrate, and a reminding component connected with the detecting component, wherein:
the detecting component is configured to detect a stretch degree of the substrate; and
the reminding component is configured to transmit a reminding signal when the stretch degree of the substrate, detected by the detecting component, meets a preset condition;
wherein the substrate is further provided with a plurality of micro-needles on a surface thereof for contact with a human body, and each of the plurality of micro-needles comprises at least one shell and one or more medicines surrounded by the at least one shell, wherein:
one or more layers where the one or more medicines are located are different from at least one layer where the at least one shell is located, and the at least one layer where the at least one shell is located is separate from and does not contain the one or more medicines;
a material of the at least one shell comprises a nanometer fiber; a material of the substrate is same as the material of the at least one shell; and the nanometer fiber is degraded when the human body produces lactic acid or pyruvate, or the nanometer fiber is decomposed in an environment inside the human body;
each of the plurality of micro-needles is configured, when puncturing into skin, to enable at least a part of the at least one shell to be hydrolyzed so that the one or more medicines in the at least one shell contacts with tissue fluid of the human body;
the smart patch further comprising one of (a), (b), (c), or (d):
(a) wherein the at least one shell comprises one shell, and the one or more medicines arranged in the one shell of each of the plurality of micro-needles is one medicine;
(b) wherein the at least one shell comprises one shell, a first medicine of the one or more medicines is arranged in the at least one shell of a part of the plurality of micro-needles, and a second medicine of the one or more medicines is arranged in the at least one shell of a remaining part of the plurality of micro-needles, wherein the first medicine and the second medicine are different medicines;
(c) wherein the at least one shell comprises two shells which are a first shell and a second shell located inside the first shell, wherein the first medicine of the one or more medicines is arranged between the first shell and the second shell, and the second medicine of the one or more medicines is arranged in the second shell, wherein the first medicine and the second medicine are different medicines; or (d) wherein the at least one shell comprises three shells, which are a first shell, a second shell located inside the first shell and a third shell located inside the second shell, wherein the first medicine of the one or more medicines is arranged between the first shell and the second shell, a transition chamber is arranged between the second shell and the third shell, and the second medicine of the one or more medicines is arranged in the third shell,
wherein the first medicine and the second medicine are different medicines.

2. The smart patch according to claim 1, wherein:
the detecting component is configured to have a resistance increasing as the substrate is being stretched, to detect the stretch degree of the substrate; and
the reminding component is configured to transmit the reminding signal when the resistance exceeds a first preset value, and/or the resistance has exceeded a second preset value for a time length longer than a preset time length, wherein the first preset value is more than the second preset value.

3. The smart patch according to claim 2, wherein the detecting component comprises a piezo-resistive pressure sensor.

4. The smart patch according to claim 1, wherein, when the smart patch comprises one of (b), (c), or (d), the first medicine is a water absorbing medicine, and the second medicine is an anti-inflammatory medicine.

5. The smart patch according to claim 1, wherein a shape of each of the plurality of micro-needles is a triangular pyramid, a rectangular pyramid, or a circular cone, wherein a bottom of the triangular pyramid, the rectangular pyramid, or the circular cone contacts with a bottom of the substrate.

6. The smart patch according to claim 1, wherein a length of each of the plurality of micro-needles in a direction perpendicular to the substrate ranges from 100 µm to 200 µm.

7. A method for fabricating the smart patch according to claim 1, the method comprising:
forming the substrate; and
forming the detecting component on the substrate, and the reminding component connected with the detecting component.

8. The method according to claim 7, wherein the forming the substrate comprises:
pouring nanometer cellulose dispersion liquid into a first mold having an array of hollow micro-needles;
inserting a second mold having a corresponding array of micro-needles into the first mold containing the nanometer cellulose dispersion liquid, keeping a preset distance between the second mold and the first mold in a vertical direction, and drying and shaping the nanometer cellulose dispersion liquid, wherein the second mold is provided with pads respectively on two sides of a frame thereof so that the preset distance is kept between the second mold and the first mold in the vertical direction when the second mold is arranged opposite to the first mold;
removing the second mold;
placing the one or more medicines into cavities of the plurality of micro-needles formed by the shaped nanometer cellulose dispersion liquid, and drying the one or more medicines;
pouring nanometer cellulose solution, and mold-pressing and drying the nanometer cellulose solution using a planar third mold; and
removing the third mold and the first mold.

* * * * *